United States Patent [19]

Pohndorf et al.

[11] Patent Number: 5,776,178
[45] Date of Patent: Jul. 7, 1998

[54] MEDICAL ELECTRICAL LEAD WITH SURFACE TREATMENT FOR ENHANCED FIXATION

[75] Inventors: Peter J. Pohndorf, Stillwater; Linda L. Lach, Vadnais Heights; Mark Holle, Blaine; Terrell M. Williams, Brooklyn Park, all of Minn.

[73] Assignee: Medtronic, Inc., Minneapolis, Minn.

[21] Appl. No.: 604,215

[22] Filed: Feb. 21, 1996

[51] Int. Cl.$^6$ .................................................. A61N 1/05
[52] U.S. Cl. ........................................ 607/127; 607/120
[58] Field of Search ..................... 128/642; 607/119–122, 607/126–128, 130–131; 600/374, 375

[56] References Cited

U.S. PATENT DOCUMENTS

| | | | |
|---|---|---|---|
| 4,827,940 | 5/1989 | Mayer et al. | 607/131 |
| 4,876,109 | 10/1989 | Mayer et al. | |
| 4,919,891 | 4/1990 | Yafuso et al. | |
| 5,049,138 | 9/1991 | Chevalier et al. | |
| 5,103,837 | 4/1992 | Weidlich et al. | 607/120 |
| 5,217,028 | 6/1993 | Dutcher et al. | 607/120 |
| 5,255,693 | 10/1993 | Dutcher et al. | 607/120 |
| 5,324,324 | 6/1994 | Vachon et al. | |
| 5,374,287 | 12/1994 | Rubin | 607/131 |
| 5,447,533 | 9/1995 | Vachon et al. | 607/120 |

*Primary Examiner*—Brian Casler
*Assistant Examiner*—George R. Evanisko
*Attorney, Agent, or Firm*—Michael J. Jaro; Harold Patton

[57] ABSTRACT

A medical electrical lead having a fixation helix which is surface treated along at least a portion to have a relatively high microscopic area along with a relatively low macroscopic area. In the preferred embodiment, such a surface treated portion is accomplished with a porous platinized construction. The surface treated portion further has a bioabsorbable coating in order to permit the helix to be inserted into the heart tissue without causing damage to the heart tissue through the engagement of the surface treated portion with heart tissue during insertion. In the preferred embodiment the bioabsorbable material is mannitol, although other bioabsorbable materials may also be used, such as a material which is no more than sparingly soluble in water, for example, the steroid beclomethasone dipropionate anhydrous. Through such a construction the helix may be inserted into tissue while the coating of absorbable materials provides a smooth surface between the surface treated portion of the helix and the tissue. Once inserted, the coating is absorbed and the surface treated portion provides electrical contact with the heart tissue.

19 Claims, 4 Drawing Sheets

MEDICAL ELECTRICAL LEAD WITH SURFACE TREATMENT FOR ENHANCED FIXATION

FIELD OF THE INVENTION

This invention relates to the field of medical electrical leads, and in particular to an active fixation medical electrical lead having a helix which is surface treated to provide enhanced electrical characteristics as well as to enhance fixation but which further features an absorbable coating to minimize tissue damage during insertion of the surface treated helix into tissue.

BACKGROUND OF THE INVENTION

In the medical field, various types of body-implantable leads are known and used. Cardiac pulse generators, in particular, use implanted leads to both sense cardiac function and deliver stimulation pulses. One type of commonly used implantable lead is an endocardial lead.

Endocardial leads are attached at their proximal end to an implantable pulse generator and at their distal end to the endocardium of a cardiac chamber. Often the lead assembly is inserted into the heart through a vein. The lead generally has an inner conductor covered by an insulative sheath.

The distal end of an endocardial lead may engage the endocardium by either an active fixation mechanism or a passive fixation mechanism. Passive fixation mechanisms, such as a tine assembly, lodge or passively fix the lead to the heart. Active fixation mechanisms use a structure, such as a helix or hook, to engage into or actively fix themselves to the heart.

A sharpened helix has been found to provide a reasonably secure means for fixing the lead to the heart. An exposed sharpened helix may damage a vein, however, during introduction. Thus many active fixation leads have helixes which either retract into the lead body or are shielded during introduction. See for example, U.S. Pat. No. 4,972,848 of Di Domenico (helix shielded within lead body which may be extended to engage cardiac tissue); U.S. Pat. No. 5,003,992 of Holleman et al. (plunger through helix guards against damage to tissue by the helix and may be retracted to engage cardiac tissue) and U.S. Pat. No. 4,827,940 of Mayer et al. (soluble cover shields helix until positioned proximate fixation site.) Among the most preferred methods of shielding a helix is where the helix may be retracted within or extended from the lead body.

Once the helix is extended from the body it is screwed into the body tissue, i.e. the myocardium, to thus fix or anchor the lead to the heart. Past designs of medical electrical leads favored a polished metal helix. In particular, polished platinum helixes were used so as to be able to be screwed into the tissue without undue friction between the helix and tissue. A roughed surface of the helix, after all, would tend to drag through the tissue and damage the myocardium.

Besides anchoring the lead, a sharpened helix, because it is inserted into the myocardium, may also be used to function as an electrode. As an electrode, however, a helix must satisfy conflicting design requirements.

First, in order to function as an electrode, the helix must provide adequate sensing as well as pacing. One currently favored approach to provide these dual function is utilize an electrode which has a relatively small macroscopic area with a relatively large microscopic area. Such an electrode may be provided using porous platinum coated over its external surface with a plating of platinum black. Such a design, moreover, also tends to promote tissue in growth into the electrode and thus would also provide enhanced fixation.

On the other hand, because an electrode must be introduced into the cardiac tissue, a roughened surface on the helix, such as that presented by a porous coating, would tend to unduly damage cardiac tissue.

In view of these competing design requirements past designs of pacing leads have tended to sacrifice electrical performance in order to minimize tissue damage. Thus many past designs of medical electrical leads featured fixation helices which have a relatively smooth surface, such as polished platinum.

SUMMARY OF THE INVENTION

It is thus an object of the present invention to provide an active fixation medical electrical lead having a helix which is surface treated to provide enhanced electrical characteristics.

It is a still further object of the present invention to provide an active fixation medical electrical lead having a helix which is surface treated to also promote tissue in growth and thus to enhance fixation.

It is a still further object of the present invention to provide an active fixation medical electrical lead having an absorbable coating to minimize tissue damage during insertion of the surface treated helix into tissue.

Briefly, the above and further objects and features of the present invention are realized by providing a medical electrical lead having active fixation which has a helix which is surface treated to provide enhanced electrical characteristics as well as to enhance fixation but which further features an absorbable coating to minimize tissue damage during insertion of the surface treated helix into tissue. In particular the present invention is a medical electrical lead having a fixation helix which is surface treated along at least a portion to have a relatively high microscopic area along with a relatively low macroscopic area. In the preferred embodiment, such a surface treated portion is accomplished with a porous platinized construction. The surface treated portion further has a bioabsorbable coating in order to permit the helix to be inserted into the heart tissue without causing damage to the heart tissue through the engagement of the surface treated portion with heart tissue during insertion. In the preferred embodiment the bioabsorbable material is mannitol, although other bioabsorbable materials may also be used, such as a material which is no more than sparingly soluble in water, for example, the steroid beclomethasone dipropionate anhydrous. Through such a construction the helix may be inserted into tissue while the coating of absorbable materials provides a smooth surface between the surface treated portion of the helix and the tissue. Once inserted, the coating is absorbed and the surface treated portion provides electrical contact with the heart tissue.

BRIEF DESCRIPTION OF THE DRAWINGS

The above and other options, features and advantages of the present invention will be more apparent from the following more particular description thereof, presented in conjunction with accompanying drawings, wherein.

3

Figure 3:
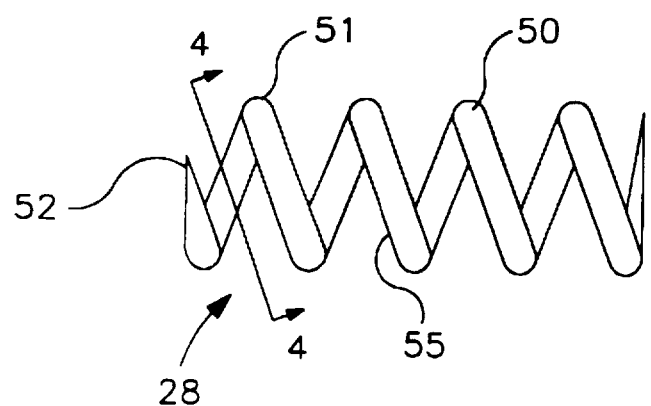

FIG. 3 is a detailed view of the helix used in the present invention.

Figure 4:
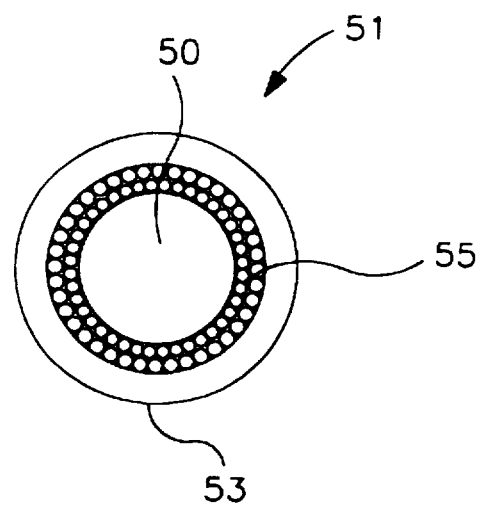

FIG. 4 is a cross sectional view of the helix along the line 4—4 of FIG. 3.

Figure 5:
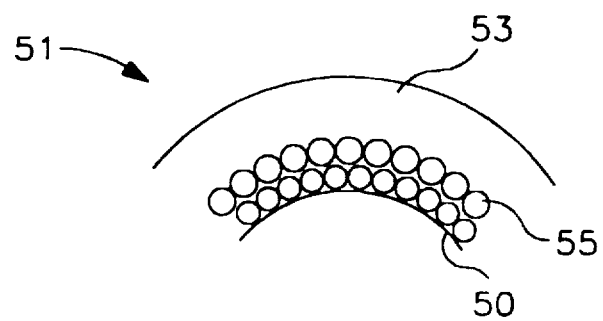

FIG. 5 depicts the helix immediately after it has been screwed into the cardiac tissue and the surface treated portion still has the coating in place.

Figure 6:
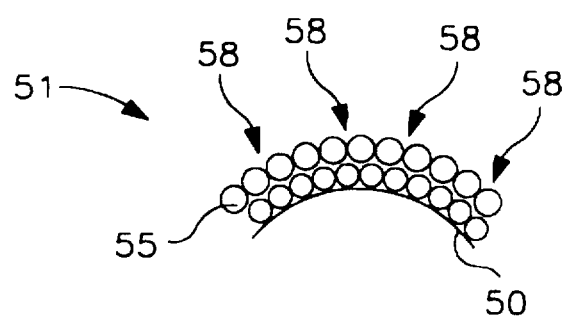

FIG. 6 depicts the helix a period of time after FIG. 5 illustrates, and thus shows the helix screwed into the cardiac tissue and the surface treated portion still has had the coating removed by the body.

Figure 7:
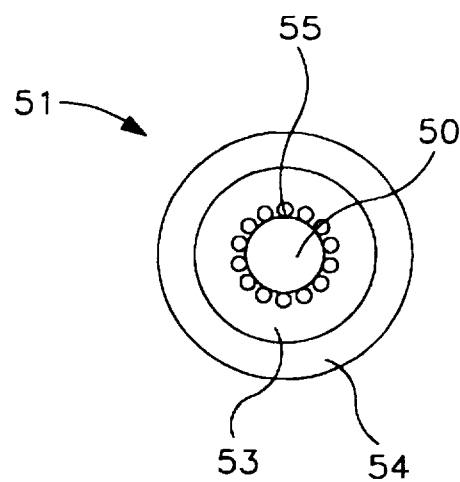

FIG. 7 is a cross sectional view of a helix used in an alternate embodiment of the present invention.

The drawings are not necessarily to scale.

DETAILED DESCRIPTION OF THE DRAWINGS

For the purposes of this specification and claims, the term "lead" is used herein in its broadest sense and includes a stimulation lead, a sensing lead, a combination thereof or any other elongated member, such as a catheter, which may usefully be introduced into a body.

Figure 1:
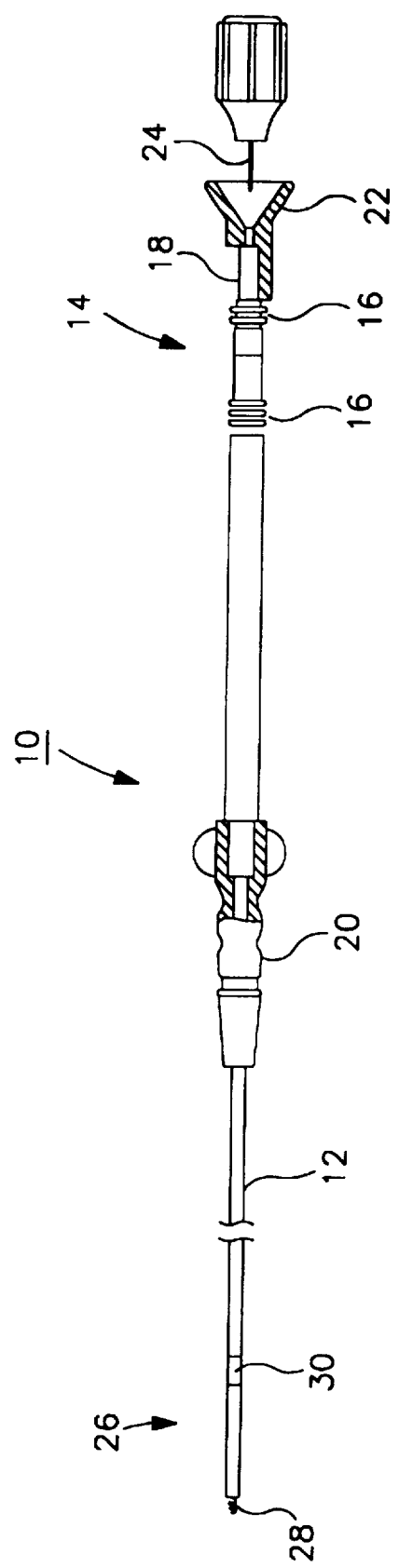
FIG. 1 is a plan view bipolar transvenous medical electrical lead in accordance with one embodiment of the invention.

Referring to FIG. 1, there is a plan view of a lead 10 according to the present invention. As seen, lead 10 has a flexible, elongate lead body 12 covered by an insulative sleeve, such as polyurethane or silicone rubber. Terminal assembly 14 is provided at the proximal end for coupling lead 10 to an implantable pulse generator (not shown.) Terminal assembly 14 has sealing rings 16 and terminal pin 18, all of a type known in the art.

An anchoring sleeve 20 (shown partially in cross-section) may also be provided for suturing lead body 12 to body tissue. Anchoring sleeve 20 and terminal assembly 14 are preferably fabricated from silicone rubber, although they may also be constructed of any other suitable biocompatible material known in the art.

Lead 10 may also include stylet guide 22 and stylet assembly 24 coupled to terminal pin 18 for imparting stiffness to lead 10 during placement. Stylet guide 22 and stylet assembly 24 are typically discarded after use and before connection of terminal pin 18 to a pacemaker pulse generator.

With continued reference to FIG. 1, an electrode and fixation assembly designated generally as 26 is disposed at the distal end of lead body 12. Electrode and fixation assembly 26 is, in the disclosed embodiment, of the bipolar type and has helix 28 at its distal end and a ring electrode 30 spaced proximally back from the distal end. As will be appreciated by those of ordinary skill in the art, helix 28 and ring electrode 30 are coupled to separate, insulated lead conductors (not shown in FIG. 1) which extend along the length of lead body 12. Lead conductors are preferably configured as concentric multi-filar coils of MP35N or any other suitable alloy, such as a platinum-iridium alloy. This configuration allows for a longitudinal lumen to exist along the length of lead body 12, such that a stylet may be received therein.

Figure 2:
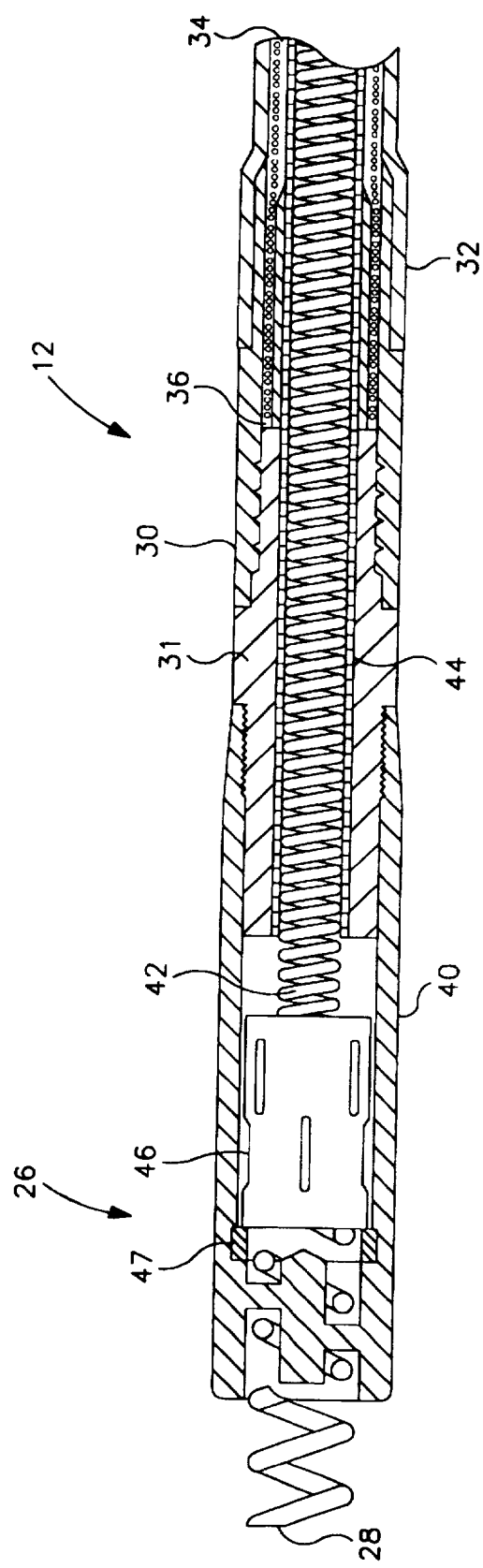
FIG. 2 is a greatly enlarged side cross-sectional view of a distal segment of the lead of FIG. 1 including the electrode assembly of the lead.

In FIG. 2, there is shown a greatly enlarged cross-sectional side view of a distal portion of lead body 12 and electrode and fixation assembly 26. As seen, lead body 12 has an outer flexible insulative sheath 32 made of silicone rubber, polyurethane, or the like. Outer insulative sheath 32 covers first coiled conductor 34. Conductor 34 extends along through lead body 12 and terminates at its distal end where it is electrically coupled, for example by spot or laser welding, to a crimp sleeve 36 made of stainless steel or the like. Crimp sleeve 36, in turn, is in electrical connection with ring electrode 30, which is preferably made of a 90/10 platinum/iridium alloy.

Partially engaged between ring electrode 30 and helix 28 is ring/spacer assembly 31 which is coupled to tip/ring spacer 40, which is preferably made of silicone rubber. In addition to establishing a predetermined distance between ring electrode 30 and helix 28, tip/ring spacer 40 functions to define a substantially cylindrical chamber in which the remaining components are disposed as well as to define the outer surface of electrode and fixation assembly 26. In the disclosed embodiment, tip/ring spacer 40 has dimensions such that a constant lead body diameter is maintained between helix 28 and ring electrode 30.

Extending along the length of lead body 12 through crimp 36, ring electrode 30, ring/spacer assembly 31 and tip/ring spacer 40 is a second coiled conductor 42, which is insulated from outer coiled conductor 34 by inner insulative sheath 44 which, like outer sheath 32 is made of silicone rubber, polyurethane, or the like. Inner conductor 42 terminates at a substantially cylindrical crimp bus 46. Crimp bus 46, in turn is coupled to helix 28. Located distal to crimp bus 46 is indicator ring 47 to provide a radiopaque indication of how far extended helix 28 is from lead body 12.

FIG. 3 is a detailed view of the helix 28 used in the present invention. As seen helix 28 has a wire core 50 which has a surface treated portion 51 spaced apart from sharpened distal end 52. Surface treated portion 51 is designed to promote tissue in growth. In addition, as already discussed above, when helix is used as an electrode and not only to physically anchor the lead, surface treated portion 51 further provides enhance electrical characteristics.

In the preferred embodiment, surface treated portion 51 has a porous coating 55 of spherical platinum powder as is well known in the art. Although platinum is the preferred material for wire core 50 and porous coating 55, they may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others, such as a platinum core with a titanium coating, and may not be effectively used together. The limitations of specific materials for use with others is well known in the art. Moreover, although in the preferred embodiment porous coating 55 of surface treated portion 51 features spherical platinum powder, other forms of conductive particulate materials besides spherical may be used, including such forms as fines, fibers or polyhedrons.

FIG. 4 is a cross sectional view of helix 28 along the line 4—4 of FIG. 3. As discussed above, surface treated portion 51 of helix 28 also features a smoothing coating 53 over the porous coating 55 to permit the helix and especially surface treated portion 51 to easily and smoothly be screwed into tissue without the relatively rough surface of the sintered porous spherical platinum powder to unnecessarily drag through and injure the tissue. Preferably smoothing coating 53 is deposited such that it has an outer surface which conforms to the surface of helix 28, such that the helix maintains its helical outer shape even with the presence of the coating (best depicted in FIG. 3.) In the preferred embodiment smoothing coating 53 is made of mannitol or any other relatively absorbable by the body material and is deposited uniformly over surface treated portion 51.

In an alternative embodiment, smoothing coating 53 is of a compound which is no more than sparingly soluble in water so as to not immediately dissolve off the helix. It is further believed that the use of a coating which is a drug may be of particular benefit. One beneficial drug which may be used is the steroid beclomethasone dipropionate anhydrous. This steroid, in particular, is very slightly soluble in water as compared to other types of steroids used in the prior art steroid eluting leads, such as dexamethasone sodium phosphate. In addition other forms of steroids or drugs may also be used to coat the porous coating 55 of surface treated portion 51 of lead 10, including those which are sparingly soluble in water, slightly soluble in water, very slightly soluble in water, and practically insoluble in water or insoluble in water. Beclomethasone dipropionate anhydrous, for example, is very slightly soluble in water, very soluble in chloroform, or freely soluble in acetone and in alcohol. These descriptions of solubility are well known in the art and are used according to the following, well understood, definitions:

| Descriptive Term | Parts of Solvent Required for 1 Part Solute |
| --- | --- |
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Practically Insoluble, or Insoluble | 10,000 and over |

The relatively rough surface of porous coating 55 facilitates the retention of smoothing coating 53. In addition, as discussed above, the relatively rough surface of porous coating 55 further allows the in growth of tissue to enhance the anchoring or fixation of helix within the tissue. In the preferred embodiment of a lead, porous coating 55 is provided through a spherical platinum powder as is well known in the art.

Porous coating 55 of surface treated portion 51 is preferably electroplated with a material to provide a relatively high microscopic surface area, such as electroplating the porous coating 55 with platinum black. Electroplating may be accomplished in any manner suitable. The relatively rough surface of porous coating 55 together with platinum black electroplating contribute to a microscopically large surface area with a relatively small macroscopic surface area for low polarization, low source impedance and low thresholds.

FIG. 5 depicts a detailed view of the surface of the helix 28 and in particular of surface treated portion 51 immediately after it has been screwed into the cardiac tissue and the surface treated portion still has the coating in place. As seen, at this stage, smoothing coating 53 remains in place. Because smoothing coating 53 remains in position while helix 28 is screwed into tissue, surface treated portion 51, which has a relatively rough surface (as compared to smoothing coating 53) is prevented from engaging into and damaging the cardiac tissue.

Because smoothing coating 53 is absorbable, however, after a passage of time, coating is removed by the body and thus surface treated portion 51 is directly exposed to the cardiac tissue, as shown in FIG. 6 which depicts the helix a period of time after FIG. 5. As seen, at this time porous coating 55 is directly exposed to the cardiac tissue and the tissue will begin to in-grow into the porous coating 55, as represented by lines 58.

As discussed above, in a further alternate embodiment of the present invention, helix 28 may be treated with, besides mannitol which readily dissolves or is absorbed by the body, a steroid which is substantially non-soluble or non-elutable in the human body. In the preferred embodiment the steroid is beclomethasone dipropionate anhydrous, although other forms of steroids or drugs which are no more than sparingly soluble in water, including high potency drugs may also be used. A saturated solution is used. This solution is prepared using the steps of dissolving beclomethasone dipropionate anhydrous micronized into acetone until a saturated solution is formed. A suitable beclomethasone dipropionate anhydrous micronized is available from Sicor S.P.A., 20017 Rho Milano, Via Terrazzano 77, Italy. A saturated solution is recognized when additional amounts of powdered beclomethasone dipropionate anhydrous do not dissolve, but rather merely falls to the bottom of the container. A suitable acetone meets American Chemical Society specifications and is available from Fisher Scientific, 711 Forbes Avenue, Pittsburgh, PA 15219-4785.

In an alternate embodiment of the present invention a saturated solution of a no more than sparingly soluble in water drug with a solvent may be prepared using the steroid betamethasone benzoate mixed with methanol. Once prepared, such a saturated solution is applied and dried to the surface treated portion of the helix. A suitable methanol meets American Chemical Society specifications and is also available from Fisher Scientific, 711 Forbes Avenue, Pittsburgh, PA 15219-4785.

In a further alternate embodiment of the present invention a saturated solution of a no more than sparingly soluble in water drug with a solvent may be prepared using the steroid halcinonide mixed with chloroform. Once prepared, such a saturated solution is applied and dried to the surface treated portion of the helix. A suitable halcinonide may be purchased from Westwood-Squibb Pharmaceuticals Inc., 100 Forest Ave. Buffalo, NY, 14213. A suitable chloroform meets American Chemical Society specifications and is also available from Fisher Scientific, 711 Forbes Avenue, Pittsburgh, PA 15219-4785.

In a further alternate embodiment of the present invention a saturated solution of a no more than sparingly soluble in water drug with a solvent may be prepared using the steroid diflorasone diacetate mixed with methanol. Once prepared, such a saturated solution is applied and dried to the surface treated portion of the helix. A suitable diflorasone diacetate may be purchased from Dermik Laboratories Inc., 500 Arcola Rd., P.O.Box 1200, Collegeville, PA, 19426-0107.

Of course, other organic solvents as well as other drugs which are no more than sparingly soluble in water may be used as well as other steroids, such as dexamethasone dipropionate anhydrous or any other drugs which are no more than sparingly soluble in water. In addition, although a saturated solution of the very slightly soluble in water drug and solvent is preferred, other solutions which are less than saturated may also be used.

Once an acceptable solution is prepared it is applied to the surface treated portion of the helix. Finally, after the solution is applied, the surface treated portion of the helix is dried to drive off the solvent and bond the no more than sparingly soluble in water drug to the surface treated portion of the helix. Drying may be accomplished by allowing the solvent to evaporate at room temperature, although other methods may also be used. Once dried, a layer of the drug remains upon the surface of the surface treated portion of the helix, as well as within its pores.

In addition, although the alternate embodiment of the present invention features a no more than sparingly soluble in water steroid applied to either the surface treated portion of a helix, the invention may utilize any antiinflammatory agent or drug which is no more than sparingly soluble in water, including other types of steroid or drugs, including those which are sparingly soluble in water (e.g. medrysone), slightly soluble in water, very slightly soluble in water (e.g. desoximetasone, or triamcinolone), and practically insoluble in water or insoluble in water (e.g. fluoromethalone, flurandrenolide, halcinonide, desoximetasone, betamethasone benzoate, triamcinolone acetonide, diflorasone diacetate or betamethasone valerate.)

Finally in a further alternate embodiment of the present invention, surface treated portion 51 of helix may feature more than one smoothing coating, each coating having different characteristics such as absorbability within the body as well as therapeutic effect. In particular, FIG. 7 shows an alternate embodiment of the present invention. All aspects of this embodiment are the same as that discussed above but for this embodiment features a surface treated portion 51 having more than one layer of a bioabsorbable coating. As seen surface treated portion 51 has three layers, porous coating 55, first smoothing coating 53 and second coating 54. First smoothing coating 53 is less soluble in water than second coating 54. First coating 53 is beclomethasone dipropionate anhydrous while second coating 54 is mannitol. Of course other materials may be used for each coating.

While the embodiments of the present invention have been described in particular application to cardiac stimulation, the present invention may also be practiced in other electrode technologies where the aforementioned characteristics are desirable, including neurological and muscle stimulation applications, as well as other forms of treating or electrically stimulating other body tissues or organs.

Furthermore, although the invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. A medical electrical lead comprising:
    an electrical conductor having a first end and a second end;
    an insulating sleeve covering the electrical conductor between the first end and the second end; and
    a helix coupled to the first end of the electrical conductor, the helix having a distal end and surface treated portion, surface treated portion having a uniform coating of a bioabsorbable material.

2. The medical electrical lead according to claim 1 wherein the uniform coating of a bioabsorbable material is mannitol.

3. The medical electrical lead according to claim 1 wherein the uniform coating of a bioabsorbable material is a dried compound not more than sparingly soluble in water.

4. The medical electrical lead according to claim 1 wherein the surface treated portion comprises a conductive porous coating.

5. A medical electrical lead comprising:
    an electrical conductor having a first end and a second end;
    an insulating sleeve covering the electrical conductor between the first end and the second end; and
    a helix coupled to the first end of the electrical conductor, the helix having a distal end and surface treated portion, the surface treated portion having a uniform coating of an absorbable material.

6. The medical electrical lead according to claim 5 wherein the surface treated portion comprises a conductive porous coating.

7. A medical electrical lead comprising:
    an electrical conductor having a first end and a second end;
    an insulating sleeve covering the electrical conductor between the first end and the second end; and
    a helix coupled to the first end of the electrical conductor, the helix having a distal end and surface treated portion, the surface treated portion having a uniform coating of mannitol.

8. The medical electrical lead according to claim 7 wherein the surface treated portion comprises a conductive porous coating.

9. A medical electrical lead comprising:
    an electrical conductor having a first end and a second end;
    an insulating sleeve covering the electrical conductor between the first end and the second end; and
    a helix coupled to the first end of the electrical conductor, the helix having a distal end and surface treated portion, the surface treated portion having a uniform coating of a drug which is no more than sparingly soluble in water.

10. The medical electrical lead according to claim 9 wherein the surface treated portion comnprising a conductive porous coating.

11. A medical electrical lead comprising:
    an electrical conductor having a first end and a second end;
    an insulating sleeve covering the electrical conductor between the first end and the second end; and
    a helix coupled to the first end of the electrical conductor, the helix having a distal end and surface treated portion, the surface treated portion having a uniform coating of a drug which is very slightly soluble in water.

12. The medical electrical lead according to claim 11 wherein the surface treated portion comprising a conductive porous coating.

13. A medical electrical lead comprising:
    an electrical conductor having a first end and a second end;
    an insulating sleeve covering the electrical conductor between the first end and the second end; and
    a helix coupled to the first end of the electrical conductor, the helix having a distal end and surface treated portion, the surface treated portion having means for promoting the in growth of tissue and a uniform coating of ar bioabsorbable material.

14. The medical electrical lead according to claim 13 wherein the means for promoting the in growth of tissue comprises a conductive porous coating.

15. A medical electrical lead comprising:
    an electrical conductor having a first end and a second end;
    an insulating sleeve covering the electrical conductor between the first end and the second end; and a helix coupled to the first end of the electrical conductor, the helix having a distal end and surface treated portion, the surface treated portion covered by a porous conductive material, the porous conductive material covered by a uniform coating of a bioabsorbable compound.

16. The lead according to claim 15 wherein the compound is an anti-inflammatory agent.

17. The lead according to claim 16 wherein the compound is beclomethasone dipropionate anhydrous.

18. The lead according to claim 16 wherein the compound is mannitol.

19. The lead according to claim 16 wherein the surface treated portion is formed of porous metallic or other conductive materials from the class of materials consisting essentially of platinum, palladium, titanium, tantalum, rhodium, iridium, carbon, vitreous carbon and alloys, oxides and nitrides.

* * * * *